United States Patent [19]

Lamprecht

[11] Patent Number: 5,530,495
[45] Date of Patent: Jun. 25, 1996

[54] APPARATUS AND METHOD FOR PROJECTING AND RECEIVING IMAGE INFORMATION USING A SCREEN

[76] Inventor: Jürgen Lamprecht, Pfalzgrafenstrasse 24, 529072, Aachen, Germany

[21] Appl. No.: 355,654

[22] Filed: Dec. 14, 1994

[30] Foreign Application Priority Data

May 20, 1994 [DE] Germany ............ 44 17 762.3

[51] Int. Cl.⁶ .................................................. A61B 3/14
[52] U.S. Cl. ..................... 351/210; 351/205; 351/221
[58] Field of Search ............................. 351/205, 209, 351/210, 211, 221, 246

[56] References Cited

U.S. PATENT DOCUMENTS

| | | | |
|---|---|---|---|
| 3,827,789 | 8/1974 | Molner et al. | 351/210 |
| 4,568,159 | 2/1986 | Baldwin | 351/210 |
| 4,988,183 | 1/1991 | kasahara et al. | 351/210 |
| 5,094,521 | 3/1992 | Jolson et al. | 351/210 |
| 5,270,748 | 12/1993 | Katz | 351/210 |

FOREIGN PATENT DOCUMENTS

| | | |
|---|---|---|
| 0064899 | 11/1982 | European Pat. Off. |
| 4037907 | 5/1991 | Germany. |
| 0514273 | 5/1976 | U.S.S.R. ............ 351/210 |

*Primary Examiner*—William L. Sikes
*Assistant Examiner*—James A. Dudek
*Attorney, Agent, or Firm*—Meltzer, Lippe, Goldstein

[57] ABSTRACT

A device for the projection of image information comprises at least one screen 1,2 on which the image information can be displayed using a plurality of individual light spots 3,4,5. The viewer of the screen 1,2 and particularly his eye movements, can be observed by assigning a light-sensitive sensor to each light spot 6,7,8 of a certain number of light spots 6,7,8. The light sensitive sensors are connected to an evaluating device.

29 Claims, 1 Drawing Sheet

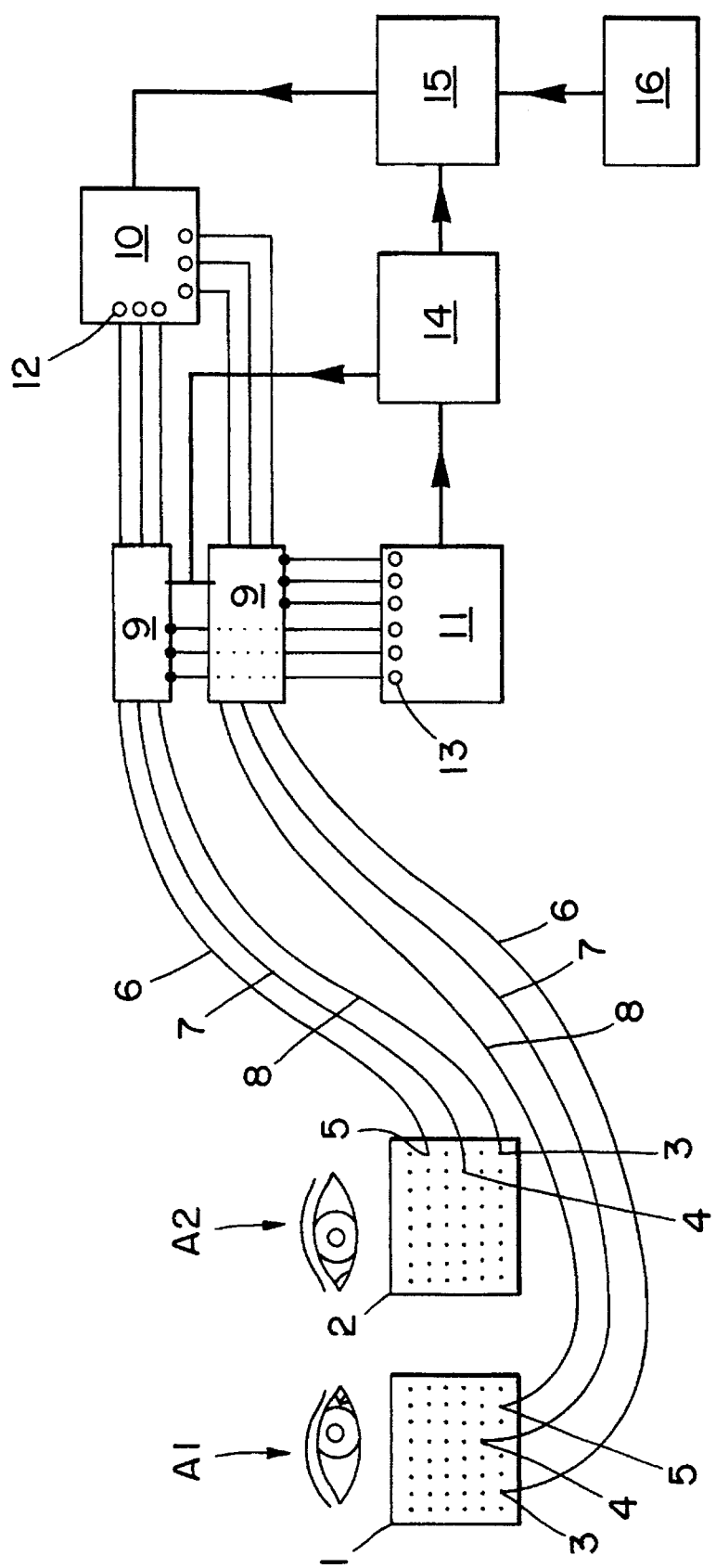

APPARATUS AND METHOD FOR PROJECTING AND RECEIVING IMAGE INFORMATION USING A SCREEN

FIELD OF INVENTION

The present invention relates to an apparatus for the projection of image information, having at least one screen on which the image information can be displayed using a plurality of individual light spots. The invention also relates to a method for the projection of image information onto screens disposed in front of the eyes of a viewer which makes use of the apparatus according to the invention.

BACKGROUND OF THE INVENTION

Apparatuses for projection of image information are used, for example, for the projection of images in virtual reality system. In these systems, the viewer wears a helmet in which a screen is disposed immediately in front of his or her eyes. Images are projected onto the screens via light wave conductors. The ends of the light wave conductors associated with the screens are disposed in the form of light spots arranged evenly in grid fashion on the surface of the screen. The totality of light spots produces a complete image, comparable with LCD screens, etc. Apart from their use in virtual reality systems, the aforementioned apparatuses are also used as monitors in conjunction with a computer or TV receiver, for example. The above mentioned applications all share the feature that it is often desirable to obtain information concerning the viewer, for example his or her eye movements or approach to the screen. This applies more particularly if such apparatuses are used for the diagnosis or therapy of people having faulty vision.

It is known in practice, for example, when the aforementioned apparatus is used in the field of medicine and therapy, to determine eye movements by means of an infrared CCD camera. The camera is connected to an evaluating device which determines the position of the axis of vision of the eye in question from the image supplied by the camera. Such cameras and evaluating devices have proved their value in practice, but their disadvantages are their size and weight and the fact that they must often be placed outside the center of the field of vision. These disadvantages are particularly noticeable if the camera is mounted with the screens in a helmet worn by a person. Moreover, in many cases a light source is required, which illuminates the observed eye. The viewer frequently finds that this additional light source disturbs his or her viewing of the screens. Finally, the miniaturization of such systems is impeded due to the large number of constructional elements required by the prior art systems.

SUMMARY OF THE INVENTION

It is an object of the invention to provide an apparatus which enables the viewer of screens of an apparatus of the kind specified to be observed by simple means, more particularly enabling the axis of vision and the movement of his or her eyes to be determined.

This problem is solved according to the invention in that each light spot of a given number of light spots is assigned a light-sensitive sensor connected to an evaluation device.

According to the invention light-sensitive sensors through which the viewer, particularly his eyes, can be observed are distributed over the entire screen surface or, alternatively, are located at least in certain areas of the screen. In that case, and particularly if the screen is carried directly in front of the eyes, the light emitted by the screen is sufficiently strong to be reflected by the eye and to be received by the light-sensitive sensors. In this manner no interfering light source is required any more in most applications in order to detect the movement of the observed eye. The corresponding signal can be transmitted to an evaluating unit which detects the eye or head position of the viewer, for example, through characteristic features from the sum of the signals of all sensors.

Correspondingly, the receiving device supplies image information concerning the viewer of the screen. In contrast with the prior art, it is no longer necessary to use independent expensive heavy and bulky cameras. Instead, the receiving device can be small in dimensions and located away from screens at a location which does not cause disturbance. Sensors possibly produced as self-contained components in combination with a light-producing element, particularly CCD sensors, can be used as the light-sensitive sensors.

In many cases it will make sense not to assign the light-sensitive sensors to a fixedly predetermined area of the screen but to use light-emitting elements which can be changed over simultaneously to be light-receiving elements to display the image information on the screen. In view of simplification of manufacture, it may, however, also be advantageous to assign a sensor connected to the evaluating unit to each light spot of a fixed number of light spots. In such a case, the sensors should be distributed at regular intervals in the form of a grid over the screen, whereby the length of the distances results from the number of light-sensitive sensors in relation to the number of light spots. In such a grid-shaped arrangement the device according to the invention supplies image information which can easily be assembled into an overall picture.

As an alternative, however, another predetermined area in which to place the light-sensitive sensors can be selected, particularly the border area of the screen. Such a configuration of the device according to the invention is advantageous, in particular when the light spot grid is relatively coarse for the display of the image information so that the image-sensitive sensors to be placed in the intervals between the image points would further coarsen the display of the image information.

A particularly advantageous embodiment of the invention is characterized in that the light spots are formed substantially by first ends of the light wave conductors. The other ends of which are connected to a projection device which feeds the light required to display the image information into the light wave conductors. The light-sensitive sensors are placed at a distance from the screen in one direction of reception and each light-sensitive sensor is assigned the end of one light wave conductor, the other end of which ends on the screen.

In such a device, and during the projection of the image information, a proportion of the light wave conductors are not used for transmitting light to the screen, but the light wave conductors transmit the incident light, for example, reflected from the viewer's face or eye to a receiving device. The receiving device has light-sensitive sensors and is, therefore, comparable to a chip camera.

The number of light wave conductors connected to the receiving device can be fixed. In that case, the ends of the light wave conductors connected to the receiving device which are associated with the screen are arranged grid-fashion at regular distances. The size of the grid is obtained from the number of light wave conductors connected to the receiving device, referred to the number of light wave conductors connected to the projection device. With such a grid-shaped arrangement the apparatus according to the invention supplies image information which can readily be combined to give an overall image.

Alternatively, the light wave conductors can be optionally connected to the projection device or the receiving device. This always makes sense, if only the part of the screen which supplies the portion of the viewer's face which is most important for the particular application is to be used for observing the viewer.

Any disturbance of the image displayed on the screen by light wave conductors which are not illuminated, since they are connected to the receiving device, can be obviated by the feature that the light wave conductors can be connected to the projection device or the receiving device in dependence on the intensity or color of the light to be supplied to the particular light wave conductor. Due to this feature of the invention, those light wave conductors to which very little if any light has been supplied and whose associated light spots, therefore, appear black, are used for transmitting the incident light reflected from the viewer's face to the receiving device. Moreover, any disturbance of the displayed image can be obviated by the feature that in each case those light wave conductors can be connected to the receiving device whose ends associated with the screen lie outside the particular field of vision of the viewer.

In the case of correspondingly rapid changeover times not perceived by the eye, disturbance to the image displayed on the screen can also be obviated by the feature that the light wave conductors can be connected in alternating sequence with the projection device and the receiving device. In such a case, if necessary, the whole screen can be used for observation. This can be used more particularly for the first determination of the position of the axis of vision, prior to the actual operation of the apparatus.

Fixed areas, particularly the marginal area of the screen, can also be used for observing the eye. This feature can be used on its own or in addition to the aforementioned, as well as other ways of utilizing the light wave conductors for the conduction of light received.

According to another feature of the invention, two screens can be positioned in front of the two eyes of a viewer. This enables the viewer's two eyes to be observed separately. This possibility of observing the eyes separately enables the inventive apparatus to be used for medical diagnosis and therapy. This application can be further extended by connecting the receiving device to an evaluating device which determines the position of the eye viewing the screen from the signals of the receiving device. The same thing applies if the projection device is connected to an image generating device which generates for each of the screens an image corresponding to the particular position of the eye. An apparatus thus constructed enables, for example, people who squint or suffer from involuntary uncontrollable eye movements to project images on to the screens disposed in front of their eyes so that a person having a squint receives the impression of stereoscopic images, such as those perceived by a person having a normal sense of vision, or that a person affected by involuntary eye movements no longer suffers from the subjectively sensed movement of his or her surroundings.

If the eye movements of a person are to be observed, permanent continuous observation can be advantageously ensured, with the arrangement of one of the screens of the apparatus according to the invention in front of each of the eyes of the viewer. In a first step the particular screen area which is least well perceived by the eyes, and/or the blind (unseeing) spot of each of the eyes, is determined. Then the light wave conductors of those light spots which are not perceived by the particular eye, having regard to its viewing direction, are connected to the receiving device by their ends which are remote from the screen. To prevent disturbance of the image perceived by the viewer which is caused by the time required for the processing of the image information and the generation of fresh images, the number of light wave conductors connected to the receiving device is always smaller than the number of light spots which corresponds to the screen surface which is only weakly perceived by the eye.

This feature reliably prevents the field of vision of the viewer from being overlapped by that zone of the area of light spots which have not yet been introduced and whose light wave conductors are still connected to the receiving device.

BRIEF DESCRIPTION OF THE DRAWINGS

The sole drawing shows diagrammatically the apparatus for projecting and receiving image information by means of a screen according to the invention.

DETAILED DESCRIPTION OF THE INVENTION

According to the figure, arranged in a helmet or correspondingly spectacles (not shown) which are placed on the head of a person having a squint or other fault of vision are image screens 1, 2 which are positioned in front of the person's eyes A1, A2. Each of the screens 1, 2 has a large number of light spots, e.g., 3, 4, 5, disposed in grid fashion and mainly formed by the ends of light wave conductors, e.g., 6. 7, 8. The other ends of the light wave conductors 6, 7, 8 are connected to optical switchover devices 9. By means of the switchover devices 9 the light wave conductors 6, 7, 8 can be connected to a projection device 10 or a receiving device 11.

The projection device 10 has opto-electrical elements 12 by which light can be supplied to the light wave conductors 6, 7, 8 so that an overall image perceived as a unit by the viewer is produced on the screens 1, 2. In contrast, the receiving device 11 has light-sensitive sensors 13 which convert the light reflected by the eyes A1, A2 to the light wave conductors into electric signals. These signals are delivered to an evaluating device 14 which determines the position of the axis of vision of the particular eye A1, A2 from the signals.

Based on the result of this evaluation, an image generating device 15 connected to the evaluating device 14 generates items of image information, for example, using images originating, from a video recorder 16. At the same time the images are converted for the screens 1, 2, so that the viewer perceives a portion of the image corresponding to that portion of the image which a viewer without a fault of vision would see. The images generated are projected by the projection device 10 onto the screens 1, 2. In addition to the image generating device 15, the result of the evaluation is also conveyed by the evaluating device 14 to the switchover devices 9.

The apparatus according to the invention operates as follows: When the helmet with the screens 1, 2 has been placed on the viewer's head, a number of tests are made to determine the area, as a rule located at the periphery of the screens 1,2, which is perceived only weakly by the eye in question or the position of the blind (unseeing) spot for each of the viewer's eyes A1, A2. The location of this spot is stored as screen coordinates in the switchover device 9. The projection device 10 then projects image information via the light wave conductors on to the screens 1, 2. At the same time the switchover device 9 always connects those light wave conductors to the receiving device 11 which are situated in a zone of the screens not perceived by the particular eye A1, A2, due to the blind spot. The evaluating device 14 continuously determines from the signals of the receiving device 11 the particular position of the eyes A1, A2 and passes the corresponding values on to the image generating device 15 and the switchover devices 9. The image generating device 15 generates corresponding items of image information for the screens 1, 2, while the switchover devices 9 connect the light wave conductors 6, 7, 8 to the projection device 10 or the receiving device 11, allowing for the previously determined location of the blind spot. If the viewer's perception is affected by disturbances caused by the time required for the evaluation and generation of the image information, the viewer can independently reduce the size of the area of the screens 1, 2 used for the observation of the eyes A1, A2.

I claim:

1. A device for the generation of image information and for observing movement of a viewer's eye, comprising at least one screen on which the image information can be displayed, a plurality of individual light spots on said at least one screen for displaying said image information, an evaluating device and a plurality of light sensitive sensors connected to said evaluating device, wherein each of said plurality of light sensitive sensors is assigned to each light spot of a given number of said plurality of light spots, each of said light sensitive sensors being placed on said at least one screen for receiving light reflected from said viewer's eye.

2. The device of claim 1, wherein each light-sensitive sensor is assigned to each light spot of a fixed number of said plurality of light spots.

3. The device of claim 2, wherein said light-sensitive sensors are arranged as a grid having regular intervals and the length of said grid results from number of light-sensitive sensors in relation to number of light spots.

4. The device of claim 1, wherein each of said plurality of light-sensitive sensors is assigned to a fixed area of said screen.

5. The device of claim 3, wherein each of said plurality of light-sensitive sensors is assigned to a fixed area of said screen.

6. The device of claim 4, wherein said fixed area is a border area of said screen.

7. The device of claim 5, wherein said fixed area is a border area of said screen.

8. The device of claim 1, further comprising a plurality of light wave conductors having first and second ends, a projection device and a receiving device, wherein said first ends of said light wave conductors form said plurality of light spots and said second ends are connected to said projection device, said projection device feeds light required to display the image information into said light wave conductors, said light-sensitive sensors are placed at a distance from said screen in said receiving device, and each of said plurality of light-sensitive sensors is associated with one of said second ends of said plurality of light wave conductors.

9. The device of claim 3, further comprising a plurality of light wave conductors having first and second ends, a projection device and a receiving device, wherein said first ends of said light wave conductors form said plurality of light spots and said second ends are connected to said projection device, said projection device feeds light required to display the image information into said light wave conductors, said light-sensitive sensors are placed at a distance from said screen in said receiving device, and each of said plurality of light-sensitive sensors is associated with one of said second ends of said plurality of light wave conductors.

10. The device of claim 8, wherein said light wave conductors can be selectively connected to said projection device or to said light-sensitive sensors of the receiving device.

11. The device of claim 9, wherein said light wave conductors can be selectively connected to said projection device or to said light-sensitive sensors of the receiving device.

12. The device of claim 10, wherein said light wave conductors are selectively connected to said projection device or said receiving device depending on strength or color of light to be fed into the appertaining light wave conductor.

13. The device of claim 11, wherein said light wave conductors are selectively connected to said projection device or said receiving device depending on strength or color of light to be fed into the appertaining light wave conductor.

14. The device of claim 10, wherein said light wave conductors having first ends lying outside a viewer's field of vision are connected to said receiving device.

15. The device of claim 11, wherein said light wave conductors having first ends lying outside a viewer's field of vision are connected to said receiving device.

16. The device of claim 12, wherein said light wave conductors having first ends lying outside a viewer's field of vision are connected to said receiving device.

17. The device of claim 13, wherein said light wave conductors having first ends lying outside a viewer's field of vision are connected to said receiving device.

18. The device of claim 10, wherein said light wave conductors are connected in alternating sequence to said projection device and to said receiving device.

19. The device of claim 11, wherein said light wave conductors are connected in alternating sequence to said projection device and to said receiving device.

20. The device according to claim 1, further comprising two screens, wherein each of said two screens is positioned before an eye of a viewer.

21. The device according to claim 3, further comprising two screens, wherein each of said two screens is positioned before an eye of a viewer.

22. The device according to claim 1, wherein said evaluating device detects position of an eye viewing the screen from signals received from said light-sensitive sensors.

23. The device according to claim 3, wherein said evaluating device detects position of an eye viewing the screen from signals received from said light-sensitive sensors.

24. The device of claim 20, further comprising an image generating device connected to said projection device wherein said image generating device produces an image for each of said screens and said image corresponds to current position of said eyes.

25. The device of claim 21, further comprising an image generating device connected to said projection device wherein said image generating device produces an image for each of said screens and said image corresponds to current position of said eyes.

26. The device of claim 22, further comprising an image generating device connected to said projection device wherein said image generating device produces an image for each of said screens and said image corresponds to current position of each said eye.

27. The device of claim 23, further comprising an image generating device connected to said projection device wherein said image generating device produces an image for each of said screens and said image corresponds to current position of each said eye.

28. Process for projecting image information on screens having a plurality of light spots which are placed before a viewer's eyes comprising, determining a screen area in which a number of said light spots are not perceived by said viewer's eyes, and connecting light wave conductors associated with said light spots not perceived by said viewer's eyes to a receiving device.

29. The process as in claim 28, wherein the number of light wave conductors connected to said receiving device is always less than the number of light spots required to constitute size of said screen area.

* * * * *